United States Patent [19]
Lee et al.

[11] Patent Number: 5,789,585
[45] Date of Patent: Aug. 4, 1998

[54] AZA CROWN ETHER COMPOUNDS AS ANION RECEPTORS

[75] Inventors: Hung Sui Lee, East Setauket; Xiao-Oing Yang, Port Jefferson Station; James McBreen, Bellport, all of N.Y.

[73] Assignee: Brookhaven Science Associates LLC, Upton, N.Y.

[21] Appl. No.: 862,734

[22] Filed: May 23, 1997

Related U.S. Application Data

[62] Division of Ser. No. 492,201, Jun. 19, 1995, Pat. No. 5,705,689.

[51] Int. Cl.$^6$ .................... C07D 225/00; C07D 295/00; H01M 2/38; H01M 8/08; H01M 8/14
[52] U.S. Cl. .................... 540/450; 429/46; 429/51
[58] Field of Search .................... 540/450; 429/51, 429/46

[56] References Cited

U.S. PATENT DOCUMENTS

| | | | |
|---|---|---|---|
| 2,349,851 | 5/1944 | Dreyfus | 564/106 |
| 3,130,224 | 4/1964 | Sugino et al. | 564/106 |
| 3,427,320 | 2/1969 | Ogden | 564/106 X |
| 3,944,526 | 3/1976 | Kray | 564/106 X |
| 4,721,770 | 1/1988 | Stockinger et al. | 528/109 |
| 4,899,249 | 2/1990 | Reilly et al. | 361/317 |
| 5,021,308 | 6/1991 | Armand et al. | 429/194 |
| 5,130,211 | 7/1992 | Wilkinson et al. | 429/198 |
| 5,141,827 | 8/1992 | Fritz et al. | 429/191 |
| 5,162,175 | 11/1992 | Visco et al. | 429/192 |
| 5,162,177 | 11/1992 | Armand et al. | 429/194 |
| 5,169,736 | 12/1992 | Bittihn et al. | 429/192 |
| 5,260,145 | 11/1993 | Armand et al. | 429/50 |
| 5,705,689 | 1/1998 | Lee et al. | 562/873 |

FOREIGN PATENT DOCUMENTS

| | | | |
|---|---|---|---|
| 0645182 | 9/1992 | Australia | 564/95 |
| 6088047 | 9/1983 | European Pat. Off. | 564/106 |

OTHER PUBLICATIONS

Dietrich, Pure & Appl. Chem., vol. 65, pp. 1457 to 1464, (1993).
Lee et al I, Proc. 4$^{th}$ Intern. Symp. on Polymer Electrolytes, BNL-60409, (1994).
Lee et al II, Proc. 4$^{th}$ Intern. Symp. on Polymer Electrolytes BNL-60409 Abstract, (1994).
Lee et al III, The Electrochemical Society, Inc. Proc. of ECS 186$^{th}$ Meeting, BNL-60924, (1994).
Costa et al, J. ElectroAnal. Chem., vol. 351, pp. 259 to 269, (1993).

*Primary Examiner*—Floyd D. Higel
*Attorney, Agent, or Firm*—Margaret C. Bogosian

[57] ABSTRACT

A family of aza-ether based compounds including linear, multi-branched and aza-crown ethers is provided. When added to non-aqueous battery electrolytes, the new family of aza-ether based compounds acts as neutral receptors to complex the anion moiety of the electrolyte salt thereby increasing the conductivity and the transference number of $Li^+$ ion in alkali metal batteries.

1 Claim, 3 Drawing Sheets

AZA CROWN ETHER COMPOUNDS AS ANION RECEPTORS

This is a divisional of application Ser. No. 08/492,201 filed Jun. 19, 1995, now U.S. Pat. No. 5,705,689.

This invention was made with Government support under contract number DE-AC02-76CH00016, between the U.S. Department of Energy and Associated Universities, Inc. The Government has certain rights in the invention.

BACKGROUND OF THE INVENTION

This invention relates to the design, synthesis, and application of a new family of aza-ether based compounds which act as anion receptors in non-aqueous battery electrolytes. As a result, the anion receptors of the present invention can be used as additives to enhance the ionic conductivity and cation transference number of non-aqueous battery electrolytes. More specifically, the new family of aza-ether based compounds includes substituted linear aza-ethers, multi-branched aza-ethers, and aza-crown ethers wherein the hydrogens on the N are substituted with an R group. R is an electron withdrawing group such as $CF_3SO_2$, $CF_3CO$, $CN$, or $SO_2CN$. The electron deficient N centers can complex anions very effectively.

Considerable research has been conducted on the design and synthesis of receptor molecules for the selective complexation of ions. While compounds which serve as cation receptors have been studied widely, information on host molecules for anions has been scarce. For example, U.S. Pat. No. 5,130,211 to Wilkinson, et al. describes an electrochemical cell which has an electrolyte solution containing an organic solvent, an alkali metal salt and at least one sequestering agent. The sequestering agent described by Wilkinson, et al., can be a glyme, crown ether or cryptand. The sequestering agents disclosed by Wilkinson, et al. are useful in complexing with the alkali moiety of the electrolyte salt and thus, act as cation complexing agents.

Dietrich (B. Dietrich, J. Pure and Appl. Chem. 65, 1457 (1993)) has reviewed the field of anion receptors and has pointed out that the requirements for anion receptors are different than those for cation receptors. This is because of the larger size of the anions and the wide variety of shapes encountered in polyatomic anions. At present, two categories of anion receptors have been developed. One includes host molecules that contain positively charged sites, the others are neutrally charged anion receptors. For the first category, the positively charged sites such as ammonium or guanidinium binding sites act as large cations and can only be used in aqueous solutions where the anions are already dissociated. These types of anion receptors cannot be used in non-aqueous electrolytes to increase ion dissociation. In the second category, the anion binding depends on either hydrogen bonding or electron deficient Lewis acid metal centers (Sn, Hg, B, or Si) in organic structures. Although these neutral receptors are useful as selective anion binding sites in both aqueous and non-aqueous solutions, they are not suitable for use in aprotic non-aqueous electrolytes. Receptors which utilize hydrogen bonding will react with lithium or sodium and will thus degrade both the anode and the electrolyte. The Lewis acid type receptors often contain heavy metals and as a result tailoring of a structure to fit various anions is difficult. Furthermore, their electrochemical stability is unknown and the released metals from decomposition would be deleterious in a battery electrolyte. The anion receptors of the present invention are a new type of neutral receptors. The novel feature of these receptors is that the anion binding is accomplished neither through a metal Lewis acid center nor through hydrogen bonding, but through an electron deficient center at N atoms that is induced by the substitution of the amine hydrogens with electron withdrawing groups. The receptors are electrochemically stable and can be easily designed to fit various anion sizes and shapes. Their chemistry is compatible with that of electrodes, salts, and solvents commonly used in non-aqueous battery electrolytes.

Moreover, in the past, inorganic, cost effective salts such as LiCl and LiBr have not been used as electrolyte salts because of their low solubility and conductivity. LiI has been used as an electrolyte to some extent because LiI has higher conductivity than LiCl and LiBr. However, $I^-$ is oxidized above 2.5 volts vs. Li so it could only be used in low voltage primary batteries such as $Li/FeS_2$.

Accordingly, there is still a need in the art of alkali metal batteries and especially lithium batteries for electrolyte additives which can complex anions, yet are stable in alkali metal and especially lithium batteries. There is also a need in the art of alkali metal batteries to enhance the conductivity of inexpensive and environmentally friendly inorganic salts such as LiCl, LiBr and LiI. In addition, there is a need to increase the transference number of the $Li^+$ ion. In many non-aqueous electrolytes, in particular polymer electrolytes, the transference number of the $Li^+$ ion is low. This introduces additional polarization losses in batteries and reduces the utilization of the cathode material.

It is therefore, an object of the present invention to provide a new family of compounds which enhances the conductivity of alkali metal battery electrolytes by complexing with the anion moiety of the electrolyte salt and also by increasing the transference number of the $Li^+$ ion.

Another object of the present invention is to increase the conductivity of cost effective electrolyte salts such as LiCl, LiBr and LiI.

Another object of the present invention is to provide improved electrochemical cells by use of electrolyte additives.

SUMMARY OF THE PRESENT INVENTION

The present invention, which addresses the needs of the prior art, provides a new family of aza-ether based compounds which act as anion receptors in non-aqueous battery electrolytes. When added to non-aqueous electrolytes, the neutral receptors of the present invention complex the anion moiety of the electrolyte salt, thereby increasing the conductivity of and the transference number of $Li^+$ ion in alkali metal batteries. The present invention also provides methods of making electrochemical cells including aza-ether anion receptors as electrolyte additives for both primary and secondary batteries. Electrolyte solvents useful for the electrochemical cells of the present invention include organic solvents such as tetrahydrofuran, polymer and gel electrolytes including a solution of lithium salt.

As a result of the present invention, stable anion receptor compounds are provided which increase dramatically the conductivity of electrolytes for alkali metal and especially lithium batteries. The electrolyte conductivity is increased because the aza-ether based compounds of the present invention complex anion moieties, non-aqueous electrolytes thereby increasing the concentration of alkali cations available for transport. As a result of using the anion receptor of the present invention alkali metal batteries are provided which have significantly increased rate capability or discharge current density. The enhanced batteries of the present invention also have increased cathode utilization because of the increased Li+ ion transference number.

Moreover, when added to liquid, non-aqueous electrolytes containing salts such as LiCl, LiBr or LiI, the aza-ether based compounds of the present invention provide a salting-in effect which results in increased solubility and electrolyte conductivity. Thus, another important advantage of using the aza-ether based compounds of the present invention is the significant cost savings resulting from using low cost electrolyte salts such as LiCl, LiBr and LiI.

Other improvements which the present invention provides over the prior art will be identified as a result of the following description which sets forth the preferred embodiments of the present invention. The description is not in any way intended to limit the scope of the present invention, but rather only to provide a working example of the present preferred embodiments. The scope of the present invention will be pointed out in the appended claims.

DETAILED DESCRIPTION OF THE INVENTION

Figure 1:
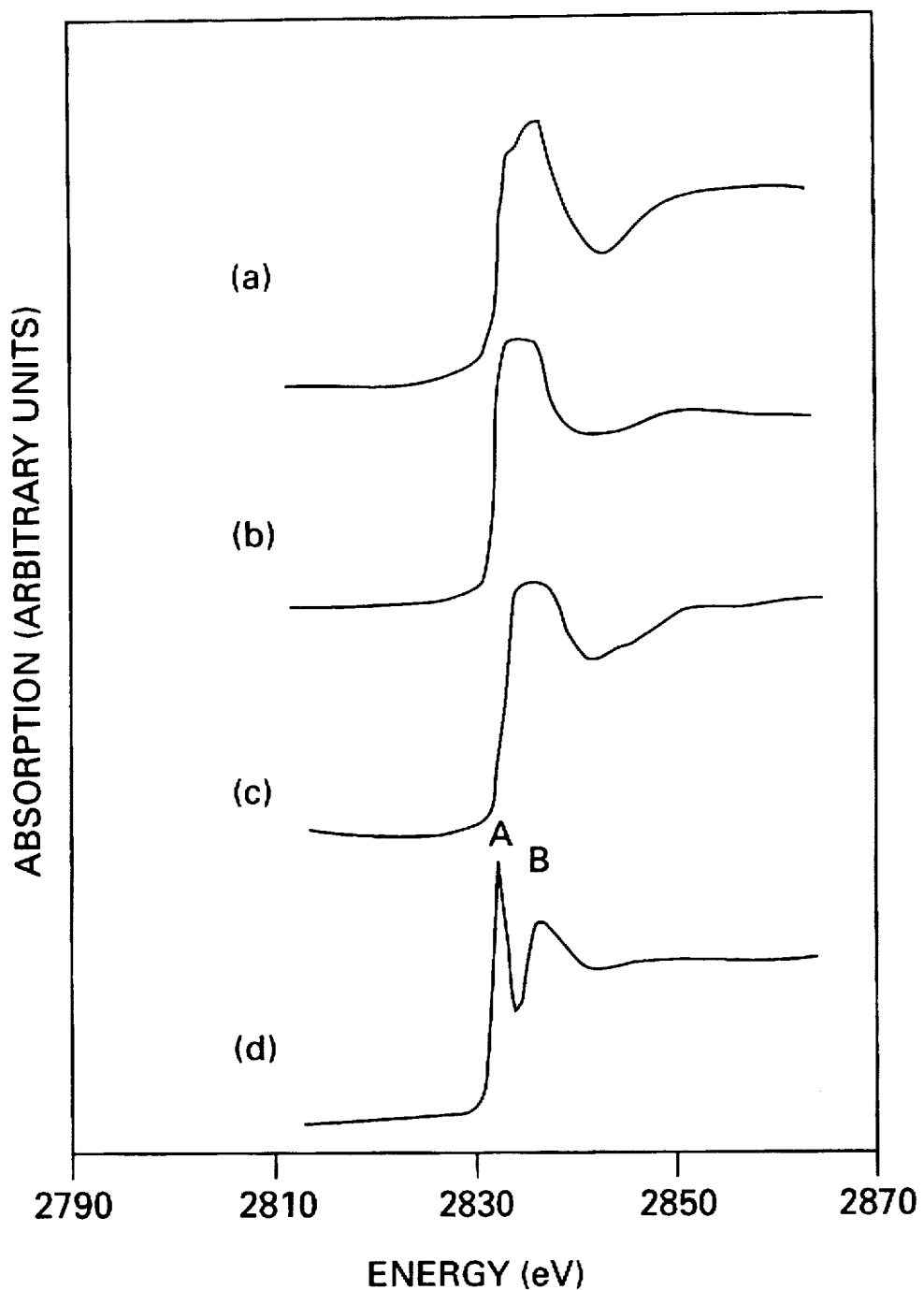
FIG. 1 illustrates near edge X-ray absorption fine structure spectra (NEXAFS) at the K edge of chlorine for (a) LiCl salt,(b) 0.2M LiCl/THF solution, (c) 0.2M LiCl+0.2M L6H in THF solution, and (d) 0.2M LiCl and 0.2M L6R in THF solution.

The present invention provides a new family of anion receptors and methods for their preparation. As used in the present invention, anion receptor means a compound which binds anions thereby moving the ionization equilibrium point of electrolyte salts towards increasing the availability of cation moieties.

The present invention also provides methods of use of these new compounds to enhance the ionic conductivity of alkali salts in non-aqueous electrolyte solutions. More specifically, the present invention provides linear aza-ethers, multi-branched aza-ethers and cyclic aza-crown ethers.

The linear aza-ethers of the present invention include compounds of the formula

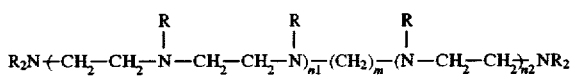

wherein $n_1=0-20$, $n_2=0-20$, $m=0-20$ and $n_1+n_2>0$ and R is an electron withdrawing group such as $CF_3SO_2$, $CF_3CO$, CN or $SO_2CN$.

Linear aza-ethers of the present invention also include compounds of the formula

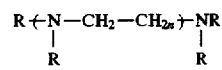

wherein $n>60$ and R is a substituent selected from the group consisting of $CF_3SO_2$, $CF_3CO$, CN and $SO_2CN$.

The multi-branched aza-ethers of the present invention include compounds of the formula $NR'_3$, $CR''_4$ wherein R' is $R_2$—N—$CH_2$—$CH_2$, R" is $R_2NCH_2CH_2NRCH_2$—, and R is a substituent selected from the group consisting of $CF_3SO_2$, $CF_3CO$, CN and $SO_2CN$.

Examples of multibranched aza-ethers are set forth below.

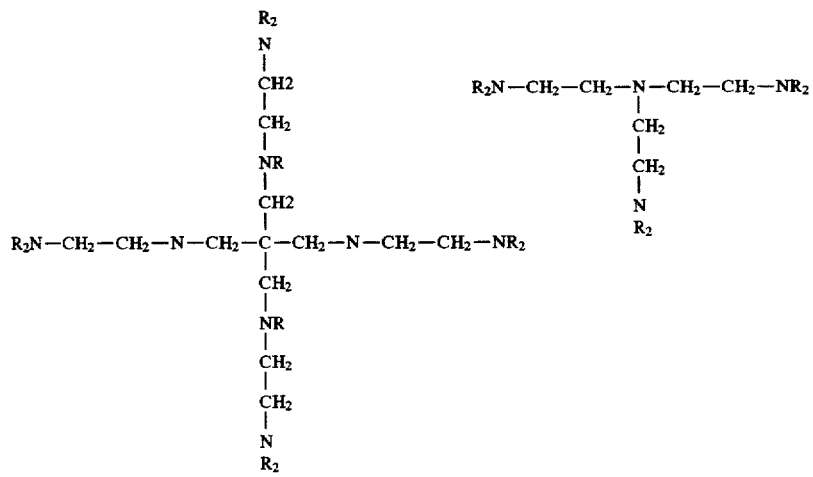

-continued

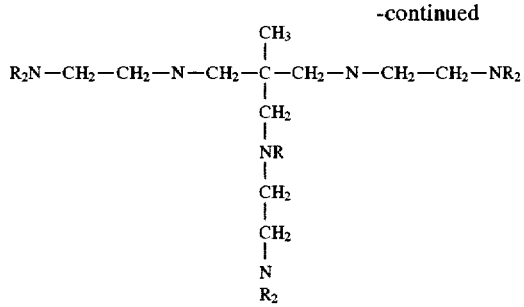

wherein R is again an electron withdrawing groups used to substitute amine hydrogen atoms, the group including $CF_3SO_2$, $CF_3CO$, CN or $SO_2CN$.

The cyclic aza crown ethers of the present invention include compounds of the formula

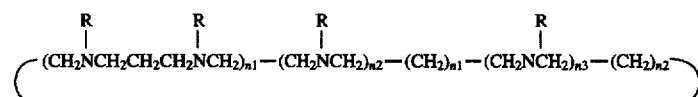

Wherein
m1, m2=0, 1, 2, 3, 4, 5;
n1, n2, n3=0, 1, 2, 3, 4, 5, 6, 7, 8, 9, 10;
n1+n2+n3>0.

OR

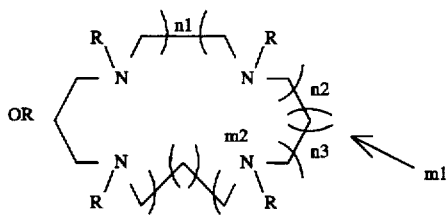

Each N has an R group thereon and R is an electron withdrawing group such as $CF_3SO_2$, $CF_3CO$, CN or $SO_2CN$.

It has been unexpectedly discovered that when the substituted aza-ether based compounds of the present invention are added to electrolytes utilized in either primary or secondary alkali metal batteries, the ionic conductivity is dramatically increased. Near Edge X-ray Absorption Fine Structure (NEXAFS) spectroscopy studies have shown that anions of alkali salts and especially lithium salts found in many electrolytes are complexed with the nitrogen groups bearing electron withdrawing groups.

Without being bound by any theory, it is believed that the aza-ether based compounds of the present invention increase electrolyte conductivity because they complex the anion moieties of electrolyte salts. Anion complexation causes an increase in the concentration and transference number of cation moieties thereby increasing the rate capability and cathode utilization of an electrochemical cell. Additionally, when used with lithium chloride, lithium bromide or lithium iodide, a salting-in effect takes place which increases the solubility of these salts. "Salting in" refers to the mutual increase in the solubilities of an electrolyte and an organic compound added to the same solvent. As a result of anion complexation properties, the new family of aza-ether based compounds of the present invention can be used as electrolyte additives in both primary and secondary batteries.

In a primary cell of the present invention other cell components include an anode composed of lithium or another alkali metal, a cathode composed of $SO_2$, CuO, CuS, $Ag_2CrO_4$, $I_2$, $PbI_2$, PbS, $SOCl_2$, $V_2O_5$, $MoO_3$ or $MnO_2$ or poly(carbon monofluoride) $(CF)n$. Because of the high solubility of lithium in aqueous solutions, non-aqueous solvents are used as electrolyte solvents. Organic solvents, such as acetonitrile and propylene carbonate and inorganic solvents, such as thionyl chloride are typical. A compatible solute such as LiI, LiBr or LiCl is added to provide the necessary electrolyte conductivity.

Organic anion lithium salts can also be used as solutes to provide electrolyte conductivity. Examples of organic anion salts include $LiSO_3CF_3$, $LiN(SO_2CF_3)_2$ and $LiC(SO_2CF_3)_3$. Other examples of organic anion salts are lithium salts with fluorinated sulfonate aromatic anions.

The aza compounds of the present invention are also effective electrolyte additives for secondary or rechargeable batteries. The secondary electrochemical cell containing the electrolyte additive of the present invention includes an alkali metal anode or an anode containing a material capable of reversibly incorporating an alkali metal, a cathode capable of reversibly incorporating an alkali metal, an alkali metal incorporated in at least one of said anode and cathode and an electrolyte. The electrolyte includes an organic solvent, a salt of the alkali metal found in either the anode or cathode and an electrolyte additive which is an anion complexing agent and can complex with the anion moiety of the electrolyte salt.

The anode material useful for the rechargeable battery of the present invention includes lithium, lithium alloys, such as Li—Al, Li—Si, Li—Cd, lithium-carbon or lithium-graphite intercalation compounds, lithium metal oxide intercalation compounds such as $Li_xWO_2$ or $LiMoO_2$ or a sulfide such as $LiTiS_2$. The anode can also be made from sodium metal or a sodium alloy such as sodium-lead.

Suitable cathode materials include transition metal oxides, metal halides or chalcogenides which intercalate lithium. Chalcogens are understood by those of ordinary skill in the art to include the chemically-related elements from Group VI of the periodic table, namely sulfur, selenium, tellurium and polonium. Preferred transition metals include manganese, nickel, iron, chromium, titanium, vanadium, molybdenum and cobalt. Preferred compositions include molybdenum sulfides, vanadium oxides and manganese oxides. $MoS_2$, $V_6O_{13}$, $Mo_6S_8$ and $MnO_2$ are more preferred, and $MnO_2$ is most preferred.

Other cathode materials useful for the electrochemical cell of the present invention include poly(carbon disulfide) polymers, organo-disulfide redox polymers, polyamine and organo-disulfide/polyaniline composites. Examples of oxides and chalcogenides useful in the present invention include: $Li_{2.5}V_6O_{13}$, $Li_{1.2}V_2O_5$, $LiCoO_2$, $LiNiO_2$, $LiMn_2O_2$, $LiMnO_2$, $Li_3NbSe_3$, $LiTiS_2$, $LiMoS_2$. Organo disulfide redox polymers are based on the reversible electrochemical dimerization/scission or polymerization/de-polymerization of organo disulfide polymers by the reaction:

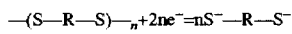

where R is an aliphatic or aromatic moiety and n>50. An example is 2,5 dimercapto-1,3,4-thiadiazole.

Cathode materials useful for sodium batteries include oxides of Ti, V, Cr, Mn, Co, Ni, Mo and sulfides of Mo, Ti and Ta. Poly(carbon disulfide) or other organo-disulfide polymers such as 2,5 dimercapto-1,3,4 thiadiazole are also suitable cathode materials for the electrochemical cells of the present invention.

It is desirable that the cathode maintain its electrical conductivity at all states of charge. Conductivity can be enhanced by adding an electrically-conductive chemically-inert material, such as a carbonaceous material like graphite or carbon black, to the cathode.

In assembling the cells of the present invention, the cathode is typically fabricated by depositing a slurry of the cathode material, the electrically conductive inert material, the binder and a fugitive liquid carrier such as cyclohexane, on the cathode-current collector, and then evaporating the carrier to leave a coherent mass in electrical contact with the current collector.

The anode can be fabricated from highly graphitic carbonaceous material in particulate form with a suitable inert polymeric binder at a level of about 2% by weight or less of polymer to anode material. Expansion and contraction of the anode during cell cycling can cause the carbonaceous particles to lose electrically conductive contact with one another. Conductivity can be similarly enhanced by adding an electrically-conductive material, such as carbon black, to the anode material.

In assembling the cell of the present invention, the anode can similarly be fabricated by depositing a slurry of the highly graphitic carbonaceous anode material, the electrically-conductive inert material, the binder and a fugitive liquid carrier such as hexane on the electrically-conductive anode support and then evaporating the carrier to leave a coherent mass in electrical contact with the support.

The cathode assembly is then combined with the anode assembly with the porous polymeric electrode separator sandwiched therebetween. The preferred way of constructing high voltage rechargeable cells is to make them by using the cathode material in the discharged state which cathode material is lithiated metal oxides, materials stable in air. Alternatively, if the cathode-active material is non-lithiated or insufficiently lithiated, then lithium either as lithium metal, alloyed lithium or intercalated lithium is incorporated in the anode in an amount that is at least sufficient to discharge the cathode material. The layered assembly is then wound around the metallic center post to form a spiral assembly which is then placed into the cell container to which is added the electrolyte solution into which the additive of the present invention has been dissolved. The cell container is then covered with a cell cap.

The electrolyte solution includes an electrolyte salt of the alkali metal exchanged between the cathode and anode dissolved in the electrolyte solvent. The electrolyte salt should be compatible with both the cathode-active material, the anode material and the aza-ether based additives of the present invention. When the alkali metal is lithium, suitable lithium electrolyte salts include $LiAsF_6$, $LiPF_6$, $LiClO_4$, $LiBF_4$, $LiSbF_6$, $LiB(C_6H_5)_4$, $LiCF_3SO_3$, $LiN(CF_3SO_2)_2$, $LiSO_3F$, $LiAlCl_4$, $LiBr$, $LiCl$, $LiI$ and mixtures thereof. $LiAsF_6$, $LiCF_3SO_3$, $LiN(CF_3SO_2)_2$ and mixtures thereof are preferred.

Suitable electrolyte solvents include non-aqueous, liquid polar solvents such as ethylene carbonate, dimethyl carbonate and mixtures thereof. Other useful solvents are cyclic and acyclic ethers, organic carbonates, lactones, formates, esters, sulfones, nitriles and oxazolidinones. Useful electrolyte solvents include tetrahydrofuran; 2-methyl furan; 4-methyldioxolane; 1,3-dioxolane; 1,2-dimethoytethane; dimethoxymethane; ethylene carbonate; propylene carbonate; γ-butyrolactone; methyl formate; sulfolane; acetonitrile; 3-methyl-2-oxazolidinone and mixtures thereof.

Polymer electrolytes of several types are also useful for electrochemical cells of the present invention. One type consists of lithium salts dissolved in linear polyethers such as poly(ethylene oxide). Because it is important that the polymer be amorphous and have a low glass transition temperature, the polymer electrolytes may be designed as polymer networks, branched or comb shaped polymers which have flexible inorganic backbones such as $(-P=N-)_n$ or $(-SiO-)_n$. A polymer electrolyte may be further modified by addition of plasticizers such as organic carbonates.

Gelled electrolytes are another type of electrolytes that are useful for the electrochemical cells of the present invention. Gelled electrolytes include a solution of lithium salt in a liquid organic solvent and a supporting matrix of a polymer such as poly(acrylo nitrile) or poly(vinylidene fluoride). Examples of lithium salts which can be used in gelled electrolytes are $LiCF_3SO_3$, $LiN(CF_3SO_2)_2$, $LiCl$, $LiBr$. Binary solvents such as mixture of ethylene carbonate and propylene carbonate can also be used as liquid solvents in gelled electrolytes.

Often blends of these solvents are used to enhance the conductivity. In addition the solvent can contain various additives. Examples are cyclic ethers and $CO_2$ to improve the cyclability of the lithium electrode, and various additives to prevent migration of sulfur from $TiS_2$ cathodes to the anode. Additives are also often added for overcharge protection and high temperature storage.

In a secondary electrochemical cell, the aza-compounds of the present invention complex the anion moieties found in the electrolyte thereby increasing the availability of the free cations. For example, in a lithium or lithium ion battery, upon leaving the anode, the lithium cation is shuttled across the electrolyte for incorporation into the host lattice of the cathode. Thus, by complexing the anion moiety, more positively charged lithium ions become available for transfer thereby increasing dramatically the ionic conductivity of the electrochemical cell.

The focus of the examples set forth below has been to provide novel syntheses for the aza compounds of the present invention. It has been unexpectedly found that by reacting an unsubstituted aza-ether with an anhydride bearing an electron withdrawing group under conditions promoting the substitution of amine hydrogens, a new family of substituted aza-ether compounds was provided. Conditions known to promote the substitution of amine hydrogen included keeping the reaction vessel under a nitrogen purge at atmospheric pressure and in a cooling bath at about −20° C. over a period of time from about 2.5 hours to about 19 hours.

NEXAFS spectroscopy studies have been conducted illustrating the efficacy of the aza family of compounds of the present invention as electrolyte additives which increase conductivity of electrolytes used in alkali electrochemical cells.

EXAMPLES

The Examples set forth below also serve to provide further appreciation of the invention but are not meant in any way to restrict the effective scope of the invention.

Example 1

Preparation of N,N,N',N',3,6-Hexa(trifluoromethylsulfonyl)-3,6-diazaoctane-1,8-diamine In this example, a linear aza anion complexing agent of the formula

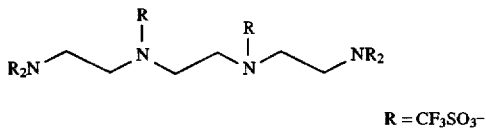

R = CF$_3$SO$_3^-$ was prepared.

40.6 g of trifluoromethane sulfonic anhydride in 30 ml of anhydrous chloroform was added to a solution of 2.92 g of triethylenetetramine and 14.5 g of triethylamine in 100 ml of chloroform, and kept under nitrogen in a cooling bath at −20° C. over a period of 2.5 hours. After stirring the mixture for 0.5 hours, the cooling bath was removed and the mixture was stirred at room temperature for 1 hour until a white precipitate formed. 11.3 g of the white precipitate was collected and washed with chloroform. After washing and drying, the chloroform filtrate was evaporated to dryness. Methanol was added to the residue and the mixture was left to stand overnight. An additional 3.9 g of precipitate was collected and combined with the crude product. The combined product was dissolved in a small amount of acetone and filtered. Methanol was slowly added to the filtrate until a crystalline product was isolated. The mixture was filtered to yield 14.2 g. of the pure product. The product had the following identification characteristics for melting point, hydrogen NMR shifts and IR absorption bands: m. p. 134°–5° C.; NMR (Acetone d$_6$), δ 4 (m, 8H), 4.5 (m, 4H), ppm; IR (KBr) 3043.7, 2998.4, 2971.7, 1457.4, 1393.3, 1202.7, 1122.3, 1009.3, 858.5, 774.1, 731.5 cm$^{-1}$.

Example 2

Preparation of N,N,N',N',3, 6-Hexa(trifluoroacetyl)-3,6-diazaoctane-1,8-diamine

In this example, another linear aza anion complexing agent was prepared. This complexing agent has the formula of

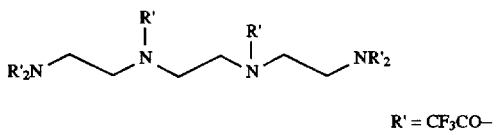

R' = CF$_3$CO—

2.19 g of triethylenetetramine in 80 ml of anhydrous chloroform was reacted at room temperature with 22.7 g of trifluoroacetic anhydride in the presence of 11.1 g of triethylamine over a period of 19 hours. The resulting white crystalline product was collected by filtration and washed with chloroform. The crude product was recrystallized from an acetone-chloroform mixture to yield 6.3 g of the pure product. The product had the following characteristics for melting point, hydrogen NMR shifts and IR absorption bands: m.p. 132°–4° C.; NMR (Acetone d$_6$), δ 3.8 (m, 8H), 4.3 (m, 4HO, ppm; IR (KBr), 2951.6, 1755.1, 1689.5, 1549, 1458.9, 1367.8, 1329.7, 1290.9, 1170.7, 1061.9, 1020.7, 921, 867.2, 751, 711.4, 634.3, 526.4 cm$^{-1}$.

The compounds in Examples 1 and 2 above are linear aza-anion complexing agents. It has been found that when used as electrolyte additives with LiCl, LiBr and LiI salts in THF as the solvent, the chain length required for anion complexation is a function of the anion size. Thus, a linear aza-compound with two nitrogens was sufficient to complex chloride ions, a linear aza-compound with three nitrogens was required to complex bromide anions and a linear aza-compound containing four nitrogens was required to complex iodide anions.

Example 3

Preparation of 1,4,8,11-Tetra(trifluoromethylsulfonyl)-1,4,8,11-tetraazacyclotetradecane In this example a cyclic aza crown compound of the formula

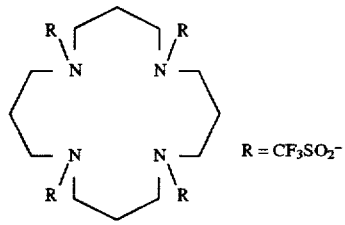

R = CF$_3$SO$_2^-$ was prepared.

11.8 g of trifluoromethane sulfonic anhydride in 20 ml of chloroform was added to a solution of 1.4 g of 1,4,8,11-tetraazacyclotetradecane in 100 ml of anhydrous chloroform, and kept in a cooling bath at −20° C. under nitrogen over a period of 50 minutes. After completing the addition, the cooling bath was removed and the mixture was stirred at room temperature for 1.5 hours. 4.3 g of precipitate was collected and washed with chloroform. The chloroform filtrate was then washed with water and dried over anhydrous magnesium sulfate to yield an additional 0.47 g of crude product. The combined crude product was recrystallized from acetone to yield 4.0 g of pure product. The product had the following characteristics for melting point, hydrogen NMR shifts and IR absorption bands: m.p. 226°–7° C.; NMR (Acetone d$_6$), δ 2.4 (m, 4H), 3.8 (m, 16H) ppm; IR (KBr) 2962.43, 2892.8, 1472.2, 1382.6, 1204.8, 1125.1, 1047.5, 975.2, 789.7, and 750.7 cm$^{-1}$.

Example 4

Preparation of 1,4,8,11-Tetra(trifluoroacetyl)-1,4,8,11-tetraazacyclotetradecane Another cyclic aza-compound of the formula

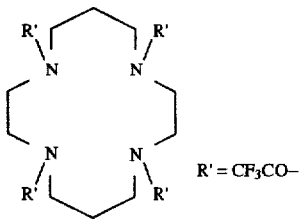

R' = CF$_3$CO— was prepared in this example.

1.2 g of 1,4,8,11-tetraazacyclotetradecane and 3.03 g of triethylamine in 100 ml of anhydrous chloroform was mixed with 6.3 g of trofluoroacetic anhydride, and kept in a cooling bath at −20° C. under nitrogen over a period of 20 minutes. The flask was removed from the cooling bath and the reaction mixture was stirred at room temperature for 2 hours. The collected precipitate was recrystallized from an acetone chloroform mixture. The pure product yield was 3.3 g and had the following characteristics for melting point, hydrogen NMR shifts and IR absorption bands: m.p. 217°–8° C.; NMR (Acetone $d_6$), δ 1.9–2.8 (m, 4H, 3.5–4 (m, 16 H) ppm; IR (KBr) 2954.4, 2903.3, 1690.2, 1524.8, 1430.8, 1372.5, 1151.9, 992.4, 865.5, 731.9 $cm^{-1}$.

The compounds synthesized in Examples 3 and 4 are crown aza-ethers based complexing agents. When used as electrolyte additives for LiCl, LiBr and LiI salts in THF as the solvent, the crown size required for complexation varies.

Example 5
Conductivity Studies

In this example the ionic conductivity of electrolyte solutions containing various aza-ether compounds of the present invention was measured and compared with the conductivity of electrolyte solution without additives. Home built conductivity cells having platinum electrodes were calibrated using 0.05N in a standard aqueous solution of potassium chloride. Conductivity measurements were made at 25° C. using a Hewlett-Packard 4129 Impedance Analyzer in the frequency range from 5 Hz to 10MHz. The ionic conductivity of solutions formed by adding various aza-ether compounds to the 0.2M LiCl/THF solutions was compared with the conductivity of LiCl-THF solution without additives. The data is summarized in Table I below. The structures of the nomenclature used in Table I are summarized in Table II below.

TABLE I

| Composition (0.2M LiCl + 0.2M aza-ether) | Conductivity (S · $cm^{-1}$) |
| --- | --- |
| LiCl | $1.6 \times 10^{-6}$ |
| LiCl + L6H | $4.2 \times 10^{-6}$ |
| LiCl + L4R | $8.4 \times 10^{-5}$ |
| LiCl + L5R | $1.4 \times 10^{-4}$ |
| LiCl + L6R | $7.2 \times 10^{-4}$ |
| LiCl + L8R | $1.4 \times 10^{-3}$ |
| LiCl + M6R | $1.7 \times 10^{-3}$ |
| LiCl + C4R | $2.3 \times 10^{-4}$ |

TABLE II

| Nomenclature | Structures |
| --- | --- |
| L6H | $H(NHCH_2CH_2)_3NH_2$ |
| L4R | $R(NRCH_2CH_2)NR_2$ |
| L5R | $R(NRCH_2CH_2)_2NR_2$ |
| L6R | $R(NRCH_2CH_2)_3NR_2$ |
| L8R | $R(NRCH_2CH_2)_5NR_2$ |
| M6R | $N(CH_2CH_3NR_2)_3$ |
| C4R | Cyclic $(CH_2RNCH_2CH_2RNCH_2)_2$ |

$R = CF_3SO_2^-$

The ionic conductivity data of Table I shows that when unsubstituted aza-ether compounds were added to a LiCl/THF solution, the increase in ionic conductivity was negligible. When aza compounds substituted with $CF_3SO_2^-$ were added to a LiCl/THF solution, the ionic conductivity increased dramatically from about one to about three orders of magnitude.

It has also been found that the ionic conductivity depended on the number of R-N groups in the anion receptor additives. The ionic conductivity increased as the number of electron withdrawing groups increased, reaching a plateau when the number of electron withdrawing groups was six. Since the R groups were strong electron withdrawing groups, a positively charged environment surrounding the nitrogen atoms was created. The resulting anion complexation would create more free $Li^+$ ions, which in turn increased the ionic conductivity of the electrolyte.

Example 6
NEXAFS Studies

In order to confirm that the anions are complexed with nitrogen atoms in R-substituted aza-ether compounds and to find out the detailed structure of the formed complexes, NEXAFS studies on single crystals of the resulting complexes were conducted.

NEXAFS measurements were made at beam line X19A of the Nationals Synchrotron Light Source. The data were collected as fluorescence excitation spectra using a large solid angle ionization chamber as the fluorescence detector. After being used in conductivity measurements, the electrolyte solutions were poured into cells with Kapton windows for NEXAFS studies. Each of these solutions were then dropped of Kapton tapes to evaporate the THF solvent for studying anion complexation in solid state. The results for electrolyte solutions are shown in FIG. 1 and the results for solids are shown in FIG. 2.

FIG. 1 shows x-ray absorption curves, at the chlorine K edge for (a) LiCl salt, (b) 0.2M LiCl/THF solution, (c) 0.2M LiCl+0.2M L6H in THF solution, and (d) 0.2M LiCl+0.2M L6R in THF solution. The "white line" peak above the edge was due to dipole-allowed transitions to final states of p symmetry. For most of the chloride salt in solid state, the white line was split into several peaks as a result of the removal of the degeneracy of the final p states due to the electric field surrounding the $Cl^-$ ions caused by the paired cations. However, the white line in curve (a) for LiCl in the solid state was a featureless broad peak. Similar structures were found for $Cl^-$ in free ion state, such as KCl in dilute aqueous solution. In curve (b), the "white line" did not change much for the LiCl salt dissolved in THF indicating that the interaction between solvent and $Cl^-$ was not strong enough to cause a splitting. In curve (c), when unsubstituted aza-ether was added into the solution, the white line structure was about the same as in curve (a) and (b), implying no complexation between this compound and the $Cl^-$ anion. In curve (d), a clear split was observed when the R-substituted aza-ether compound was added into the solution. The results shown in curve (d) constituted a strong evidence that $Cl^-$ is complexed with nitrogen atoms of the R-substituted aza-ether compounds but not with the nitrogen atoms of the unsubstituted aza-ether compounds.

Figure 2:
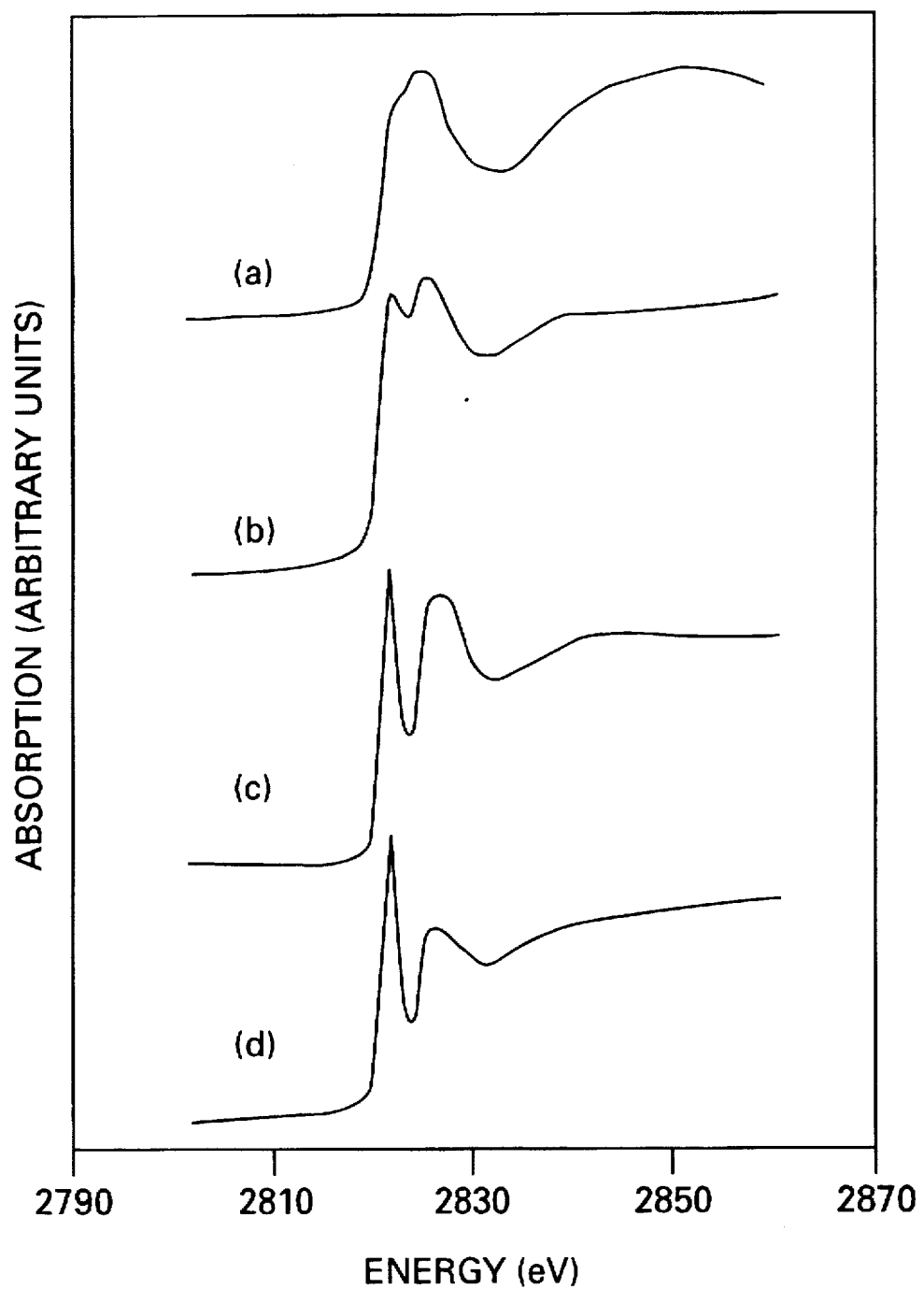
FIG. 2 illustrates NEXAFS spectra at the K edge of chlorine of solid state samples for: (a) 0.2M LiCl+0.2M L4R, (b) 0.2M LiCl+0.2M L5R, (c) 0.2M LiCl+0.2M L6R, and (d) 0.2M LiCl+0.2M L8R.

FIG. 2 shows the x-ray absorption curves at the chlorine K edge for solid samples obtained by evaporating THF solvent from mixed LiCl and R-substituted aza-ether compound solutions. The solutions used were: (a) 0.2M LiCl+ 0.2M L4R, (b) 0.2M LiCl+0.2M L5R, (c) 0.2M LiCl+0.2M L6R, and (d) 0.2M LiCl+0.2M L8R. The white line splitting depends on the number of R groups in the R-substituted aza-ether compounds complexed with $Cl^-$. It was interesting to note that the intensity of a sharp feature labeled (A) correlated with number of R groups in the added aza-ether compounds. Thus, it was noted that the higher the number of R groups the sharper the (A) feature of the white line splitting. A similar correlation existed between the ionic conductivity and the number of R groups as shown in Table I. Since all of these spectra were for samples in the solid state rather than in solution, it was concluded that stable complexes were formed in both solution and in solid state.

Figure 3:
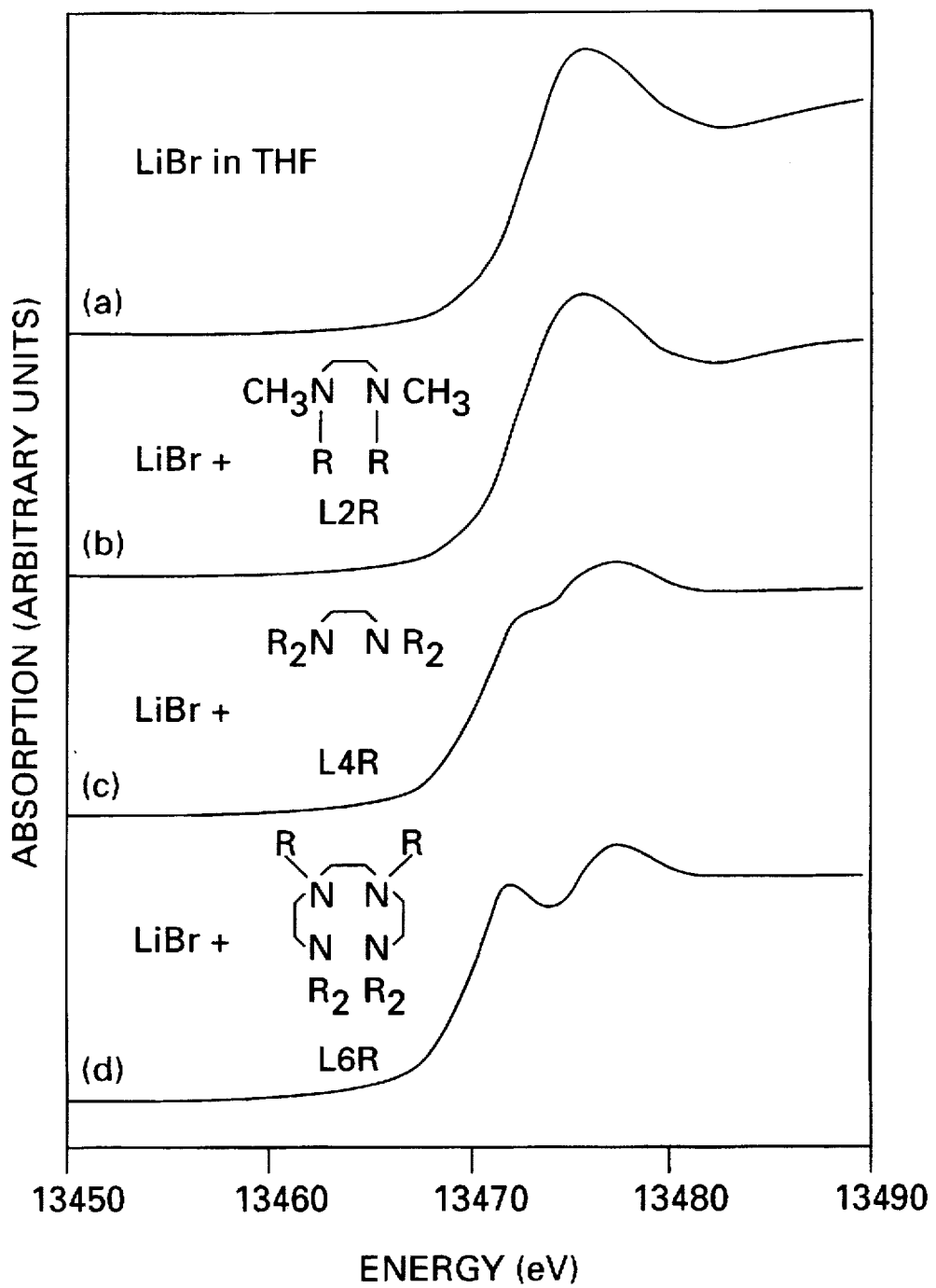
FIG. 3 illustrates NEXAFS spectra at the K edge of bromine for (a) 0.2M LiBr in THF solution, (b) 0.2M LiBr+0.2M L2R in THF solution, (c) 0.2M LiBr+L4R in THF solution, (d) 0.2M LiBr+L6R in THF solution.

FIG. 3 shows x-ray absorption curves at the bromine K edge for (a) 0.2M LiBr/THF solution, (b) 0.2M LiBr+0.2M L2R in THF solution, (c) 0.2M LiBr+0.2M L4R in THF solution, (d) 0.2M LiBr+0.2M L6R in THF solution. As was observed in the case of chloride complexation, the white line splitting for bromide depends on the number of R groups in the R-substituted aza-ether compounds complexed with $Br^-$. It was noted that for bromide containing electrolyte solutions changes in the white line appeared only when the anion receptor compound had at least three substituted nitrogens as shown by curves (c) to (d) of FIG. 3. Thus, it was found that the larger the anion, the longer the substituted aza-ether compound required to achieve desired anion complexation.

Thus, while there have been described what are presently believed to be the preferred embodiments of the present invention, those skilled in the art will appreciate that other and further modifications can be made without departing from the true scope of the invention, and it is intended to include all such modifications and changes as come within the scope of the claims as appended herein.

We claim:

1. A cyclic aza-crown ether compound of the formula

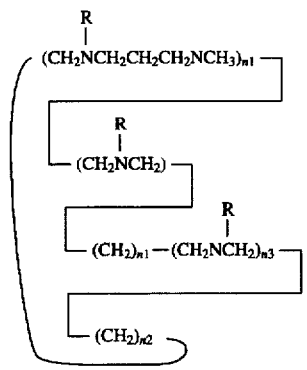

wherein
$m_1$, $m_2$=0, 1, 2, 3, 4, 5;
$n_1$, $n_2$, $n_3$=0, 1, 2, 3, 4, 5, 6, 7, 8, 9, 10; and
$n_1+n_2+n_3>0$
R is a substituent selected from the group consisting of $CF_3SO_2$, $CF_3CO$, $CN$ and $SO_2CN$.

* * * * *